(12) United States Patent
Petrov

(10) Patent No.: US 7,531,700 B2
(45) Date of Patent: *May 12, 2009

(54) FLUORINATED ARYLETHERS AND METHODS FOR USE THEREOF

(75) Inventor: Viacheslav A. Petrov, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/669,404

(22) Filed: Sep. 24, 2003

(65) Prior Publication Data

US 2005/0065382 A1  Mar. 24, 2005

(51) Int. Cl.
 *C07C 43/205* (2006.01)
 *H01L 51/50* (2006.01)

(52) U.S. Cl. .............. 568/649; 568/654; 568/656; 568/658; 428/690; 428/917; 257/40; 313/506

(58) Field of Classification Search .......... 568/610, 568/649, 655, 656, 657, 658, 630, 654; 252/301.16, 252/582, 586, 511; 257/40
See application file for complete search history.

(56) References Cited

U.S. PATENT DOCUMENTS

| | | | |
|---|---|---|---|
| 3,467,638 A | 9/1969 | Pattison | |
| 3,694,499 A | 9/1972 | Quarles, Jr. | |
| 3,926,989 A | 12/1975 | Rebsdat et al. | |
| 4,093,665 A | 6/1978 | Belous et al. | |
| 4,157,344 A | 6/1979 | Feiring | |
| 4,299,996 A | 11/1981 | Parlman et al. | |
| 4,377,711 A | 3/1983 | Rico et al. | |
| 4,575,571 A | 3/1986 | Desbois et al. | |
| 4,600,787 A | 7/1986 | Marhold et al. | |
| 4,668,830 A | 5/1987 | Desbois | |
| 4,695,657 A | 9/1987 | Desbois | |
| 4,950,802 A | 8/1990 | Nader | |
| 5,348,677 A * | 9/1994 | Poetsch et al. | 252/299.6 |
| 5,463,088 A | 10/1995 | Lui et al. | |
| 5,484,932 A | 1/1996 | Marhold | |
| 5,547,593 A * | 8/1996 | Sanechika et al. | 508/207 |
| 5,849,959 A | 12/1998 | Pfirmann et al. | |
| 6,528,165 B2 * | 3/2003 | Chandler | 428/402.2 |
| 2002/0173155 A1 * | 11/2002 | Hiromasu et al. | 438/694 |

FOREIGN PATENT DOCUMENTS

| | | | |
|---|---|---|---|
| EP | 0 638 629 A2 | | 2/1995 |
| EP | 1 318 185 A1 | * | 6/2003 |
| GB | 1230932 | * | 4/1968 |
| JP | 06-293691 | * | 10/1994 |

OTHER PUBLICATIONS

Kamal et al., Facile and efficient synthesis of fluoroalkyl aryl ethers, Aug. 2002, Tetrahedron Letters, vol. 43(41), pp. 7353-7355.*
Copending U.S. Appl. No. 10/669,403.*
Derwent abstract of JP 02227285 A, Sep. 10, 1990.*
Hirakata et al., Derwent abstract of JP 07270805A, Mar. 1994.*
JP404321638A, Patent Abstract, Production of Fluoroanisoles, Nov. 11, 1992, Asahi Glass Co. Ltd.
JP406293691A, Patent Abstract, Highly Fluorinated Phenylpropyl Ether and Its Production, Oct. 21, 1994, Kanto Denka Kogyo Co. Ltd.
H. Fukui et. al., Novel Refrigeration Lubricants for use with HFC Refrigerants, Tribology International, 2000, pp. 707-713, vol. 33.
D. Xuemei et. al., Polyfluoroalkyl Aryl Ethers, Acta Chimica Sinica, 1986, pp. 604-609, vol. 44.
V.V. Chapurkin et. al., Synthesis of Fluorinated Aryl Peroxides, Russian Journal of Organic Chemistry, 1999, p. 1551, vol. 35.
N. Yakata et. al., Unique Bioconcentration Characteristics of New Aryl Fluoroalkyl Ethers in Common Carp, 2003, pp. 153-161, vol. 51.

* cited by examiner

*Primary Examiner*—Rosalynd Keys
(74) *Attorney, Agent, or Firm*—John H. Lamming

(57) ABSTRACT

The invention provides new fluorinated solvents that have many uses. One such use is as a solvent useful in the deposition of organic active materials in the manufacture of organic electronic devices. The new fluorinated solvents are fluorinated arylethers and can be readily prepared from corresponding phenols and fluorinated olefins.

10 Claims, 1 Drawing Sheet

FLUORINATED ARYLETHERS AND METHODS FOR USE THEREOF

FIELD OF THE INVENTION

The invention relates generally to fluorinated solvents and specifically to fluorinated arylethers and methods for use thereof.

BACKGROUND INFORMATION

Organic electronic devices play an important role in industry. For example, organic light emitting diodes (OLEDs) are promising for display applications due to their high power conversion efficiency and low processing costs. Such displays are especially promising for battery-powered, portable electronic devices, including cell-phones, personal digital assistants, handheld personal computers, and DVD players. These applications call for displays with high information content, full color, and fast video rate response time in addition to low power consumption.

OLED's typically contain electroluminescent (EL) layers arranged between an anode and a cathode. Each EL layer contributes to the overall performance of the display. Thus, when manufacturing a display containing an OLED, each EL layer is carefully deposited in a controlled fashion onto a suitable underlying surface.

One cost-efficient method for deposition of EL layers in the manufacture of such displays is solution deposition. Solution deposition typically involves depositing a layer from solution using a variety of well-known techniques, such as, e.g., spin coating and ink-jetting. Efficient solution deposition depends, at least in part, on the appropriate combination of active materials, for example, light-emitting material and a solvent for the EL material. As such, one area currently drawing the attention of researchers is the identification of solvents for optimum solution deposition properties, which in turn results in cost-efficient production of devices containing OLED displays.

SUMMARY OF THE INVENTION

The Invention provides fluorinated solvents useful for solution deposition of organic active materials in the manufacture of organic electronic devices. in one embodiment, there are provided compounds having the structure:

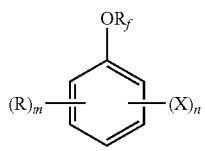

wherein:
R is $C_1$-$C_{10}$ alkyl, $C_1$-$C_{10}$ alkoxy, or $C_1$-$C_{10}$ oxyalkyl,
$R_f$ is $C_1$-$C_{10}$ fluorinated alkyl, $C_2$-$C_{10}$ fluorinated alkenyl, $C_{1\text{-}10}$ fluorinated oxyalkyl, or $C_2$-$C_{10}$ fluorinated oxyalkenyl, and
X is H, F, Cl, Br, $C_1$-$C_{10}$ alkyl, $C_1$-$C_{10}$ alkoxy, $C_1$-$C_{10}$ oxyalkyl, $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl,
m is from 1-5, and
n is from 0-4, wherein in m+n is no greater than 5.

In another embodiment, there are provided organic electronic devices having at least one organic active layer, deposited from a solution, wherein the solution comprises at least one compound having the structure:

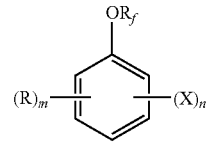

wherein:
R is $C_1$-$C_{10}$ alkyl, $C_1C_{10}$ alkoxy, or $C_1$-$C_{10}$ oxyalkyl,
$R_f$ is $C_2$-$C_{10}$ fluorinated alkyl, $C_1$-$C_{10}$ fluorinated alkenyl, $C_1$-$C_{10}$ fluorinated oxyalkyl, or $C_2$-$C_{10}$ fluorinated oxyalkenyl, and
X is H, F, Cl, Br, $C_1$-$C_{10}$ alkyl, $C_1$-$C_{10}$ alkoxy, $C_1$-$C_{10}$ oxyalkyl, $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl,
m is from 0-5, and
n is from 0-5, wherein m+n is no greater than 5.

DETAILED DESCRIPTION OF THE INVENTION

Figure 1:
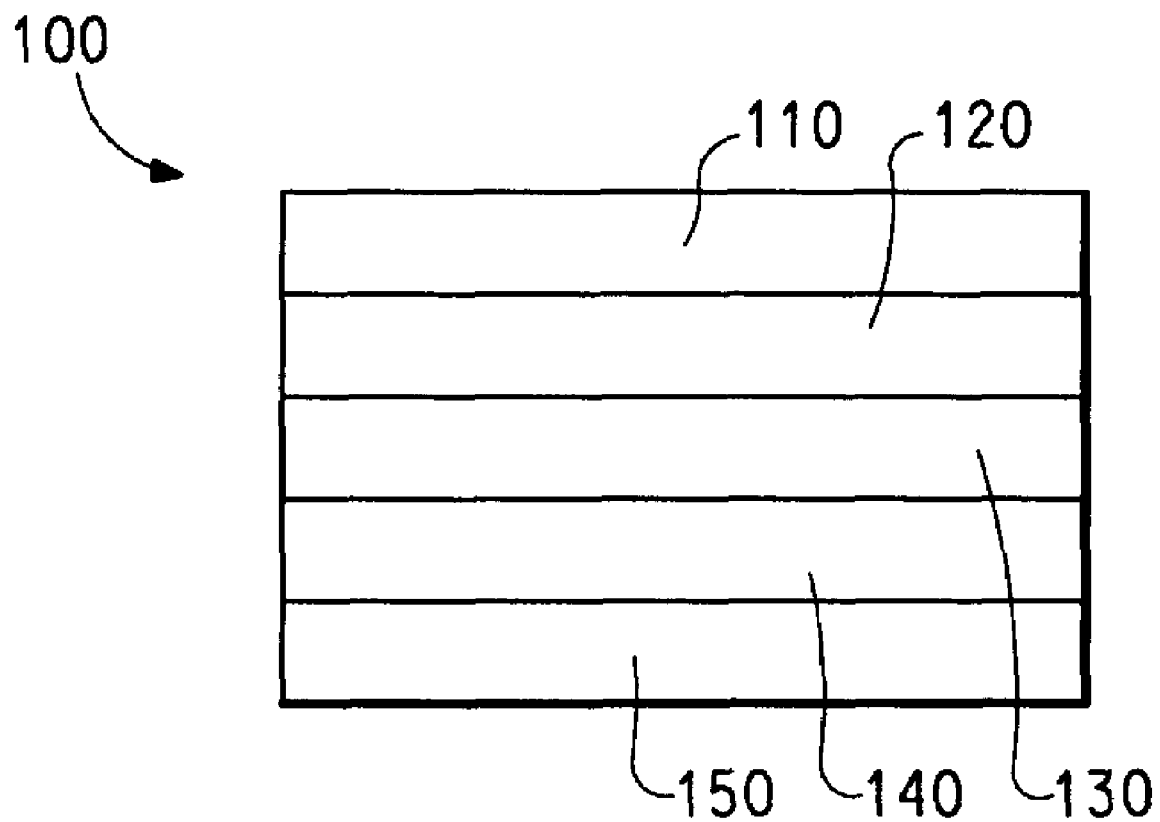
FIG. 1 is an exemplary electronic device.

It has been found that certain fluorinated arylethers are useful as solvents for solution deposition of organic active materials onto a variety of surfaces. In one embodiment, there are provided compounds having the structure:

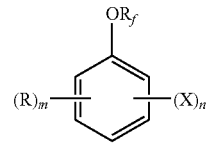

wherein:
R is $C_1$-$C_{10}$ alkyl, $C_1$-$C_{10}$ alkoxy, or $C_2$-$C_{10}$ oxyalkyl, $R_f$ is $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl, and
X is H, F, Cl, Br, $C_1$-$C_{10}$ alkyl, $C_1$-$C_{10}$ alkoxy, $C_1$-$C_{10}$ oxyalkyl, $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl,
m is from 1-5, and
n is from 0-4, wherein m+n is no greater than 5.

In the compounds of the invention, the R group is not fluorinated.

As used herein, the term "solution deposition" refers to any method for depositing a liquid medium onto a substrate only includes, but is not limited to continuous and discontinuous deposition techniques such as Gravure coating, stamping, slit-die, printing, ink-jetting, ink-dispersion, screen-printing, spin-coating, rolling, curtain coating, dipping, and extruding and other conventional techniques. As used herein, the term "liquid medium" is intended to mean a material that is predominantly a liquid, and encompasses solutions, dispersions, emulsions, and the like.

As used herein, the term "alkyl" refers to a monovalent straight or branched chain hydrocarbon group having from one to about 10 carbon atoms, including methyl, ethyl, n-propyl, isopropyl, n-butyl, isobutyl, tert-butyl, n-hexyl, and the like.

As used herein, "alkoxy" refers to the moiety —O-alkyl-, wherein alkyl is as defined above.

As used herein, "oxyalkyl" refers to alkyl moieties in which at least one —CH$_2$— unit of the alkyl moiety has been replaced by an oxygen atom.

As used herein, "alkenyl" refers to straight or branched chain hydrocarbyl groups having from 2 to about 10 carbon atoms and having one or more carbon-carbon double bonds.

As used herein, "oxyalkenyl" refers to alkenyl moieties in which at least one —CH$_2$— unit of the alkenyl moiety has been replaced by an oxygen atom.

As used herein, "fluorinated" means that at least one hydrogen atom of the alkyl, alkenyl, oxyalkyl, or oxyalkenyl moiety has been replaced with a fluorine atom.

As used herein, "perfluorinated" refers to an alkyl, alkenyl, oxyalkyl, or oxyalkenyl moiety in which each and every hydrogen atom has been replaced with a fluorine atom.

As used herein, the term "$R_f$" refers to a fluorinated group.

The IUPAC numbering system is used throughout, where the groups from the Periodic Table are numbered from left to right as 1-18 (CRC Handbook of Chemistry and Physics, 81$^{st}$ Edition, 2000).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

In some embodiments of the invention, $R_f$ is $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl.

In other embodiments, R and X are each independently $C_1$-$C_{10}$ alkyl or $C_1$-$C_{10}$ alkoxy.

In certain other embodiments, $R_f$ is a $C_1$-$C_3$ fluorinated alkyl, such as, for example, —CF$_2$CF$_2$H.

Exemplary fluorinated aryl ethers contemplated for use in the practice of the invention include, but are not limited to:

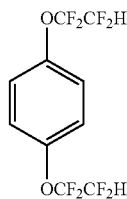

A

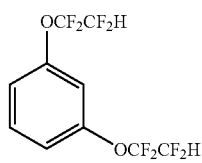

B

C

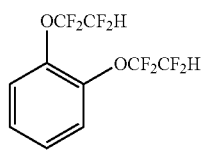

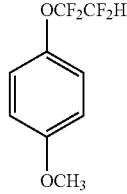

D

F

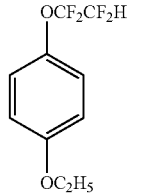

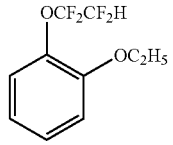

G

I

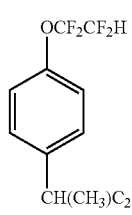

K

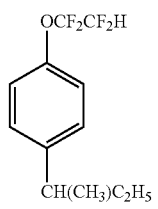

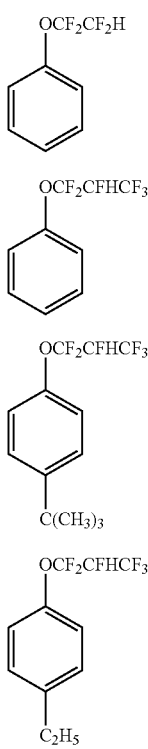

Compounds of the invention can be prepared by a variety of methods known to those skilled in the art. For example, aryl-1,1,2,2-tetrafluoroethyl ethers can be made using the procedure reported in GB Patent 1,320,648 (1973) by reacting the appropriate phenol with tetrafluoroethylene in the presence of base, in water-mixable solvent, as set forth below in Scheme 1.

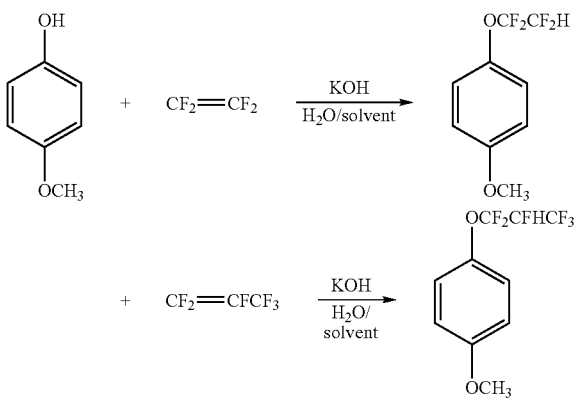

Scheme 1 depicts a reaction between a phenol and a suitable fluorinated olefin in the presence of a base catalyst, resulting in the corresponding fluorinated arylether. The reactions outlined above employ a $C_2$ and a $C_3$ fluorinated olefin, i.e., tetrafluoroethylene and hexafluoropropylene, respectively, however, it Is understood that any $C_2$-$C_{10}$ fluorinated olefin is suitable for use in preparing new fluorinated awl ethers. Aryl-1, 1, 1, 2, 3, 3-hexafluoropropyl ethers M, N and O were prepared similarly, by reading phenolic compound in the presence of base with hexafluoropropene, instead of tetrafluoroethylene. It should be pointed out, that in this case isolated product contained 6-8% of unsaturated material [$CF_3CF{=}CFOAr$], forming in the reaction as byproduct. The reaction set forth in Scheme 1 is typically carried out in polar solvents or polar solvent mixtures, such as, for example, water, water/acetonitrile, and the like. The reaction is typically carried out at a temperature of at least about 80° C. for about 10-15 hours. Reaction conditions and boiling points of polyfluorinated aryl ethers are given in Table 1 of Example 1.

The fluorinated arylethers described herein are useful for solution deposition of organic active materials onto a wide variety of substrates in organic electronic devices. Such materials can be inorganic or organic, polymers or small molecules, dyes or dopants, and can be fluorescent or phosphorescent emitters organic active or photoactive sensitive, charge (electron and hole) transport materials or buffer layer materials useful in a wide variety of organic electronic devices.

Organic electronic devices include: (1) devices that convert electrical energy into radiation (e.g., a light-emitting diode, light-emitting diode display, or diode laser), (2) devices that detect signals through electronics processes (e.g., photodetectors (e.g., photoconductive cells, photoresistors, photoswitches, phototransistors, phototubes), IR detectors), (3) devices that convert radiation into electrical energy (e.g., a photovoltaic device or solar cell), and (4) devices that include one or more electronic components that include one or more organic semi-conductor layers (e.g., a transistor or diode). By utilizing new fluorinated arylethers, these organic active materials can be deposited from solution onto surfaces of inorganic materials such as a metal or metal oxide (such as, e.g., indium/tin oxide), The organic active materials can also be deposited onto organic polymer-based materials, such as for example, polyaniline (PAni), polyethylenedioxythiophene (PEDOT), and the like.

The fluorinated arylethers described herein are useful in the manufacture of electronic devices. FIG. 1 is a schematic of an exemplary electronic device, an organic light-emitting diode (OLED) display, and layer 100 includes a photoactive layer positioned between two electrical contact layers. The electronic device 100 includes a hole transport layer 120 located between the photoactive layer 130 and an anode layer 110. An optional electron transport layer 140 is located between the photoactive layer 130 and a cathode layer 150. Depending on the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, phototubes, and photovoltaic cells, as described in Markus, John, *Electronics and Nucleonics Dictionary*, 470 and 476 (McGraw-Hill, Inc., 1966). The device is not limited with respect to system, driving method, and utility mode.

By utilizing fluorinated arylethers, the photoactive materials can be cast from solution onto the anode, typically a metal or metal oxide (such as, e.g., indium/tin oxide), or onto organic polymer-based hole transport layers, such as for example, polyaniline (PAni), olyethylenedioxythiophene (PEDOT), and the like. Alternatively, the EL materials can be cast onto the cathode or electron injection layer.

New fluorinated arylethers may be useful in other applications such as refrigerants, heat transfer media, polymerization media, particulate removal fluids, carrier fluids, buffing abrasive agents, displacement drying agents, and the like.

The invention will now be described in greater detail by reference to the following non-limiting examples.

EXAMPLES

Example 1

This Example describes a typical protocol for preparing new fluorinated arylethers. A 400 mL Hastelloy shaker tube was charged with a mixture of water, acetontrile, and KOH, and was then cooled down to −50° C. The tube was evacuated, charged with a fluorinated olefin (in the Examples set forth in Table 1, the fluorinated olefin is either tetrafluoroethylene or hexafluoropropylene; commercially available, DuPont) and maintained at a temperature of 80-150° C. for 1-14 h. The reaction mixture was then diluted with water (500-600 mL), and extracted with $CH_2Cl_2$ (100 mL). After separation the organic layer was washed with 10% NaOH solution (500 mL×3), and dried over $MgSO_4$. The solvent was removed under vacuum and the liquid residue was distilled under reduced pressure. Table 1 sets forth experimental data used to produce thirteen fluorinated arylethers according to the invention.

TABLE 1

|   |   | Phenol/olefin (mol) | Catalyst (mol) | $CH_3CN$/water (mL) | Temp. (° C.) | Time (h) | Yield (%) | B.P. (° C.)/mm Hg |
|---|---|---|---|---|---|---|---|---|
| 1 | A | 0.2/0.5 | KOH (0.17) | 50/100 | 130 | 14 | 70 | 80-81/10 |
| 2 | B | 0.2/0.5 | KOH (0.17) | 50/100 | 130 | 14 | 77 | 43-44/0.17 |
| 3 | C | 0.2/0.5 | KOH (0.17) | 50/100 | 130 | 14 | 81 | 39-40/0.1 |
| 4 | D | 0.4/0.5 | KOH (0.17) | 50/100 | 150 | 14 | 77 | 46-47/0.14 |
| 5 | E | 0.5/0.5 | KOH (0.17) | 50/100 | 150 | 14 | 68 | 18-22/0.8 |
| 6 | F | 0.4/0.5 | KOH (0.17) | 50/100 | 150 | 14 | 66 | 80-81/12 |
| 7 | G | 0.4/0.5 | KOH (0.17) | 50/100 | 150 | 14 | 45 | 24-25/0.1 |
| 8 | I | 0.4/0.5 | KOH (0.17) | 50/100 | 150 | 14 | 33 | 40/0.1 |
| 9 | K | 0.4/0.5 | KOH (0.17) | 50/100 | 150 | 14 | 53 | 42-44/0.1 |
| 10 | L | 0.5/0.5 | KOH (0.17) | 50/100 | 150 | 14 | 68 | 19-22/0.1 |
| 11 | M | 0.5/0.5 | KOH (0.17) | 50/100 | 80 | 12 | 76 | 54-55/12 |
| 12 | N | 0.2/0.2 | KOH (0.17) | 50/100 | 80 | 12 | 69 | 52/0.2 |
| 13 | O | 0.2/0.2 | KOH (0.08) | 50/100 | 80 | 12 | 63 | 38-40/0.5 |

While the invention has been described in detail with reference to certain preferred embodiments thereof, it will be understood that modifications and variations are within the spirit and scope of that which is described and claimed.

What is claimed is:

1. An organic electronic device comprising a solution of an organic active material and a compound having any one of the following structures:

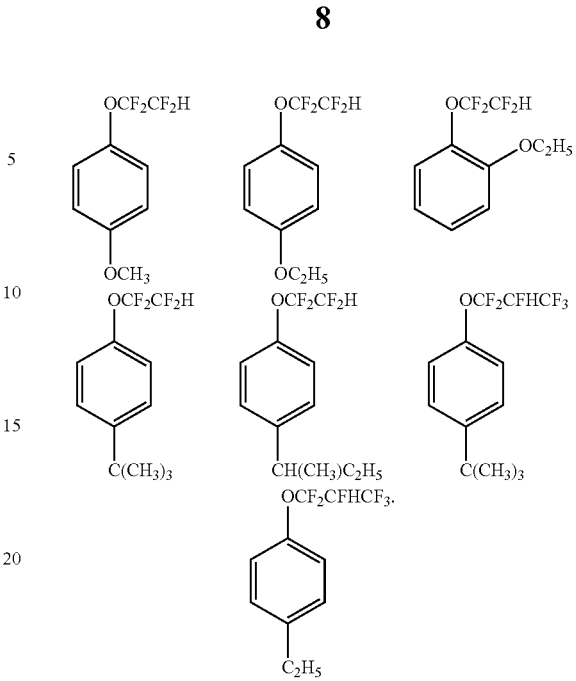

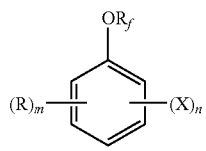

wherein the electronic device is an organic light-emitting diode.

2. An organic electronic device, comprising at least one organic active layer, wherein the at least one organic active layer is deposited from solution, wherein the solution comprises an organic active material and at least one compound having the structure:

![structure](benzene ring with $OR_f$, $(R)_m$, $(X)_n$ substituents)

wherein:
R is $C_1$-$C_{10}$ alkyl, $C_1$-$C_{10}$ alkoxy, or $C_1$-$C_{10}$ oxyalkyl,
$R_f$ is $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl, and
X is H, F, Cl, Br, $C_1$-$C_{10}$ alkyl, $C_1$-$C_{10}$ alkoxy, $C_1$-$C_{10}$ oxyalkyl, $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl,
m is from 1-5, and
n is from 0-4, wherein m+n is no greater than 5;
wherein the organic active material is selected from fluorescent emitters, phosphorescent emitters, charge transport materials and buffer layer materials, and
wherein the electronic device is selected from an organic light-emitting diode and a photodetector.

3. The device of claim 2, wherein $R_f$ is $C_1$-$C_{10}$ fluorinated alkyl, $C_2$-$C_{10}$ fluorinated alkenyl, $C_1$-$C_{10}$ fluorinated oxyalkyl or $C_2$-$C_{10}$ fluorinated oxyalkenyl.

4. The device of claim 2, wherein R and X are each independently $C_1$-$C_{10}$ alkyl or $C_1$-$C_{10}$ alkoxy.

5. The device of claim 2, wherein $R_f$ is a $C_1$-$C_3$ fluorinated alkyl.

6. A solution comprising an organic active material and a compound, wherein the organic active material is selected from fluorescent emitters and phosphorescent emitters, and the compound has the structure:

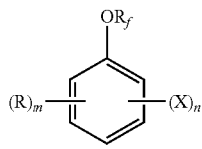

wherein:
R is $C_1$-$C_{10}$ alkyl, $C_1$-$C_{10}$ alkoxy, or $C_1$-$C_{10}$ oxyalkyl,
$R_f$ is $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl, and
X is H, F, Cl, Br, $C_1$-$C_{10}$ alkyl, $C_1$-$C_{10}$ alkoxy, $C_1$-$C_{10}$ oxyalkyl, $C_1$-$C_{10}$ fluorinated alkyl, $C_2$-$C_{10}$ fluorinated alkenyl, $C_1$-$C_{10}$ fluorinated oxyalkyl, or $C_2$-$C_{10}$ fluorinated oxyalkenyl,
m is from 1-5, and
n is from 0-4, wherein m+n is no greater than 5.

7. The solution of claim 6, wherein $R_f$ is $C_1$-$C_{10}$ fluorinated alkyl, $C_2$-$C_{10}$ fluorinated alkenyl, $C_1$-$C_{10}$ fluorinated oxyalkyl or $C_2$-$C_{10}$ fluorinated oxyalkenyl.

8. The solution of claim 6, wherein R and X are each independently $C_1$-$C_{10}$ alkyl or $C_1$-$C_{10}$ alkoxy.

9. The solution of claim 6, wherein $R_f$ is a $C_1$-$C_3$ fluorinated alkyl.

10. A solution of claim 6 wherein the compound has any one of the following structures:

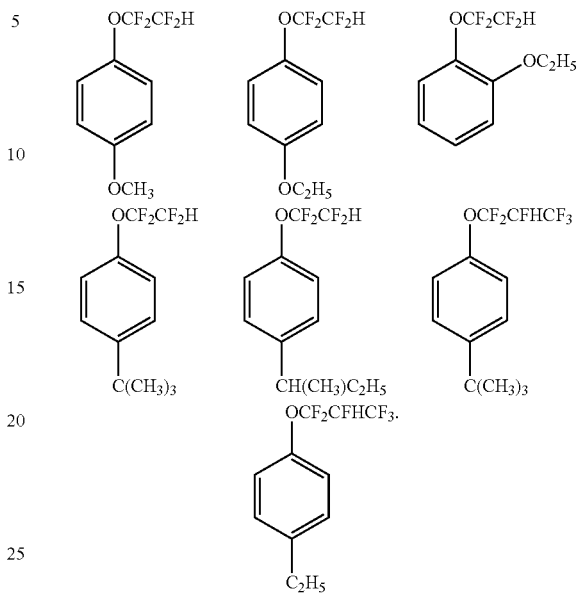

* * * * *